(12) United States Patent
Klinski et al.

(10) Patent No.: US 8,148,338 B2
(45) Date of Patent: Apr. 3, 2012

(54) DOXORUBICIN FORMULATIONS FOR ANTI-CANCER USE

(75) Inventors: Evgueni Klinski, Kirkland (CA); Kishore Patel, Lasalle (CA); Grzegorz Pietrzynski, Montreal (CA); Valery Alakhov, Baie d'Urfe (CA)

(73) Assignee: Supratek Pharma Inc. (CA)

( * ) Notice: Subject to any disclaimer, the term of this patent is extended or adjusted under 35 U.S.C. 154(b) by 547 days.

(21) Appl. No.: 11/359,352

(22) Filed: Feb. 22, 2006

(65) Prior Publication Data

US 2007/0196493 A1    Aug. 23, 2007

(51) Int. Cl.
  *A61K 31/70* (2006.01)
  *A61K 9/14* (2006.01)
(52) U.S. Cl. ............ 514/34; 514/788; 514/789
(58) Field of Classification Search .......... 424/400, 424/422, 184.1, 178, 94.1, 486, 450; 514/772.1, 514/44, 772.5–772.7, 893, 894, 908, 34, 514/788, 789; 264/4.3
See application file for complete search history.

(56) References Cited

U.S. PATENT DOCUMENTS

| | | | | |
|---|---|---|---|---|
| 4,927,571 A * | 5/1990 | Huang et al. | ................... | 264/4.3 |
| 5,091,373 A * | 2/1992 | Gatti et al. | ................ | 514/34 |
| 5,817,321 A * | 10/1998 | Alakhov et al. | .............. | 424/400 |
| 6,277,410 B1 * | 8/2001 | Kabanov et al. | ............. | 424/486 |
| 6,387,406 B1 | 5/2002 | Kabanov et al. | | |
| 2003/0157082 A1 * | 8/2003 | Hunter et al. | ................ | 424/94.1 |
| 2004/0258747 A1 * | 12/2004 | Ponzoni et al. | .............. | 424/450 |
| 2005/0119193 A1 | 6/2005 | Motoyama | | |

OTHER PUBLICATIONS

Gary K. Schwartz and Ephraim S. Casper, A Phase II trial of Doxorubicin HCl Liposome Injection in patients with advanced pancreatic adenocarcinoma, Investigational New Drugs 13, 77-82, 1995.*

The International Search Report and Written Opinion by the International Searching Authority, issued on May 17, 2007, in the PCT application No. PCT/CA2007/000182.

* cited by examiner

*Primary Examiner* — Michael G Hartley
*Assistant Examiner* — Jagadishwar Samala

(57) ABSTRACT

Doxorubicin block copolymer formulations for use in preparing injectable compositions for treating cancer patients which contain lactose for solubilizing the doxorubicin and block copolymers in said formulations and methyl paraben for stabilizing these formulations, as well as a method of preparing and using these injectable compositions.

16 Claims, No Drawings

DOXORUBICIN FORMULATIONS FOR ANTI-CANCER USE

FIELD OF INVENTION

The present invention relates to improved formulations for injectable administering doxorubicin to cancer patients and improved methods of treatment for cancer patients based upon these formulations.

BACKGROUND

Doxorubicin is a known chemotherapeutic agent administered mainly by intravenous injection to cancer suffering patients. Because of its complex structure, doxorubicin exhibits limited solubility in physiological fluids. In addition, doxorubicin is not fully transmitted across cell membranes and binds with plasma protein, as well as undergoes other non-specific interactions in the bloodstream before doxorubicin can reach the target cancer. This has caused doxorubicin to be utilized at high dosages so that a therapeutic does reaches the target cancer. Since doxorubicin has very strong side effects the use of high dosages can be very disadvantageous.

In order to avoid some of these problems doxorubicin and other chemotherapeutic agents have been formulated utilizing polyoxyethylene polypropylene block copolymer mixtures which allow the chemotherapeutic agent, particularly doxorubicin and its pharmaceutically acceptable salts, to be solubilized in aqueous medium and physiological fluids, and be effectively transported to its targets. The use of these copolymer mixtures to solubilize chemotherapeutic agents, particularly doxorubicin and its pharmaceutically acceptable salts, is disclosed in U.S. Pat. No. 5,698,529; U.S. Pat. No. 5,817,321; U.S. Pat. No. 6,060,518; U.S. Pat. No. 6,227,410 and U.S. Pat. No. 6,387,406.

The use of these block copolymers to prepare injectable solutions has been fraught with difficulty. In particularly the hydrophilic block copolymer and the hydrophobic block copolymer are waxy and adhesive solids. The handling of such materials in preparing injectable solutions is difficult, and requires special manufacturing procedures and quality control. The dissolution of such material is often slow and difficult to control. Therefore the use of waxy solid materials for precise dosing of strong biologically active compounds makes their use difficult in preparing injectable solutions for clinical practice. In addition, such solutions have to be prepared about or near the time of their use. In this regard, chemical stability of the components after reconstitution in aqueous media is often limited, and pre-made solutions are often not acceptable forms for medical use by injection.

It is therefore suggested to modify the mentioned composition with biologically non-active components to obtain an instantly soluble composition. Such modifications of injectable solutions can be difficult. Several components which could potentially be used in the formulation mixture, to accelerate the dissolution of the given composition, are not suitable for injectable solutions. The requirement that a product mixture be administered by injection limits the admixtures to only those materials which are biologically inert, stable and compatible.

Furthermore, it has been found that these compositions containing doxorubicin have limited stability and can deteriorate on standing. Therefore, once these compositions are produced they should be used for delivering doxorubicin to the patient immediately so as to avoid any decomposition. The products cannot be prepared in bulk and then later dispensed into unit injectable dosage form for administration to the patients. Once these compositions have been formulated in a liquid aqueous medium and dried, these compositions cannot be reproducibly reconstituted by the addition of water.

Therefore, it has long been desired to prepare doxorubicin as a stable liquid composition where it can be stored for long periods of time, dried and shipped and thereafter reproducibly reconstituted in a soluble form which can be administered to patients in the same therapeutic reactive form in which the composition was initially formulated.

SUMMARY OF INVENTION

In accordance with this invention it has been found that when the doxorubicin block copolymer mixture is formulated with lactose, the lactose makes this composition instantly dissolvable in water allowing the product to be dried to a solid. This solid can be reproducibly reconstituted by the addition of a sterile aqueous injectable solution to reproduce the activity of the composition before it was dried. In this manner, the lactose adds solubility to the product so that it can be stored for long periods of time as a solid and be reconstituted to an injectable form at the time of use. In addition, the doxorubicin in the composition is maintained in injectable form and maintains its solubility when injected into the blood stream. In this manner, the doxorubicin injected from this formulation possesses good transport properties, especially with regard to cell membranes so as to easily reach its target. This allows the doxorubicin administered by this formulation to be used as a chemotherapeutic agent for treating patients with better efficacy than previously.

In addition, it has been found that by the addition of methyl paraben to the formulation, preferably prior to drying, provides the formulation with enhanced stability which allows the solid thus formed to be reproducibly reconstituted later, without any loss of activity when it is administered to a patient by injection.

DETAILED DESCRIPTION

In accordance with this invention, it has been found that the addition of lactose to a doxorubicin block copolymer formulation provides solubility to the doxorubicin and the rest of the formulation so that the formulation can be dissolved in water, dried to a solid and the solid can be later reproducibly reconstituted by the addition of an aqueous injectably acceptable carrier without any loss of pharmaceutical activity. In this manner, the formulation can be first prepared in bulk and later divided into many injectable dosage forms, each containing the therapeutically effective amount of doxorubicin or salts thereof, for injection to patients. In this way the injectable formulation can be prepared in bulk, dried and shipped, and at a later time the injectable dosages can be prepared from the dried solid just prior to administration. In accordance with this invention the reconstituted solid does not lose its pharmaceutical activity and the doxorubicin in the formulation is quickly and easily solubilized in water and in physiological fluids.

The composition of this invention can be formulated by providing a mixture of doxorubicin or a pharmaceutically acceptable salt thereof, the block copolymer and lactose and, if desired to enhance stability, methyl paraben and then dissolving the mixture in water. It has been found that the lactose improves the dissolution of the composition so that it can dissolve in the aqueous medium in minute or less. The composition is prepared utilizing a predetermined amount of doxorubicin or its pharmaceutically acceptable salt. The amount may be greater or less than a therapeutically effective amount for administration to patients since the invention allows the doxorubicin formulation to be prepared in bulk or in small amounts and then later reconstituted with a solid, and the reconstituted solid be reformulated by the addition of an aqueous injectable carrier to form the solution for injection into the patient. On the other hand the composition can be formulated just prior to injection with the proper dosage of doxorubicin or its pharmaceutically acceptable salts for injectable administration.

Beneficial stabilization results are achieved, by formulating the composition, preferable either before drying or before injection, with the addition of a stabilizing amount of methyl paraben to the composition. While the use of lactose in the composition enhances the solubility of doxorubicin or its pharmaceutically acceptable salts, the use of methyl paraben tent of from about 10% to about 50% by weight of the hydrophobic copolymer and the hydrophilic copolymer has an ethylene oxide content of from about 50% to about 90% by weight of the hydrophilic copolymer. In this block copolymer mixture the weight ratio of the hydrophilic copolymer to the hydrophobic copolymer is from about 6 to about 20 parts by weight of the hydrophilic copolymer per part by weight of the hydrophobic copolymer with from about 3 to about 10 parts by weight of the hydrophilic polymer per part by weight of the hydrophobic copolymer being preferred. In formulating these compositions the copolymer mixture contains from about 5 to about 15 parts by weight of the copolymer mixture per part by weight of doxorubicin or its pharmaceutically acceptable salt in the composition.

The preferred block copolymers for use in the formulation of this invention have the formula:

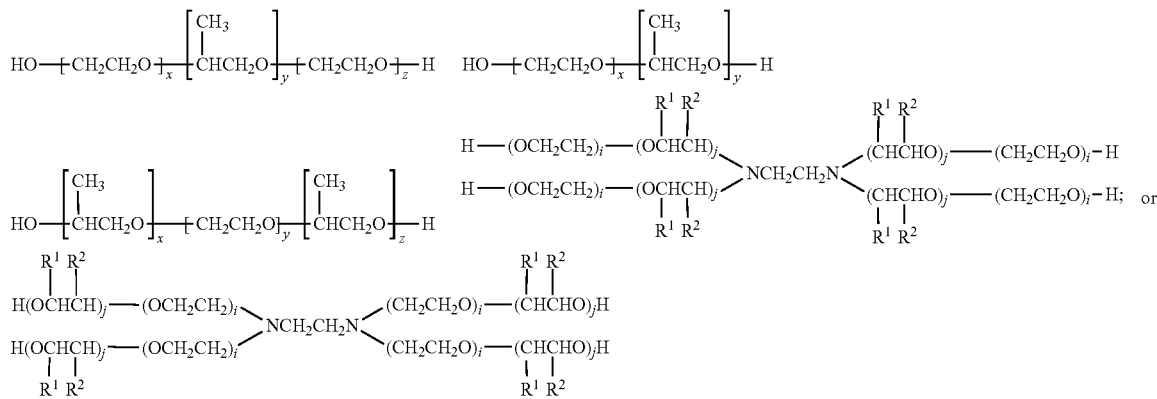

increases the stability of the formulation so that when it is dried, it can be reproducibly reconstituted long after formulation without any loss of activity of the doxorubicin or its pharmaceutically acceptable salts.

As used herein, doxorubicin includes both doxorubicin as well as its pharmaceutically acceptable salts such as the acid addition salts which include the hydrochloric acid salt.

The use of polyoxyethylene polyoxypropylene block copolymers in doxorubicin formulations has been described in the following U.S. patents:

U.S. Pat. No. 5,698,529
U.S. Pat. No. 5,819,321
U.S. Pat. No. 6,060,518
U.S. Pat. No. 6,277,410; and
U.S. Pat. No. 6,387,406.

These block copolymers can be utilized in formulations in the composition of this invention.

The two block copolymers of poly(oxyethylene)-poly(oxypropylene) polymers are chosen for their hydrophobic hydrophilic properties. The hydrophobic hydrophilic properties of a given block copolymer depends upon the ratio of the number of oxyethylene groups to the number of oxypropylene groups in the polymer, with the number of oxypropylene groups providing the polymer with a hydrophobic nature and the number of oxyethylene groups providing the hydrophilic nature of the polymer. Therefore, the more polyoxyethylene groups in the polymer the more hydrophilic is the polymer.

In accordance with this invention, two block-poly(oxypropylene)-poly(oxyethylene) polymers are used, one being a hydrophilic block copolymer and the other being a hydrophobic block copolymer. The copolymers should be chosen so that the hydrophobic copolymer has an ethylene oxide conin which x, y, z, i and j have values from about 2 to about 800, and wherein for each $R^1$, $R^2$ pair, one is hydrogen and the other is a methyl group.

In another preferred embodiment of this invention block copolymers have the formula:

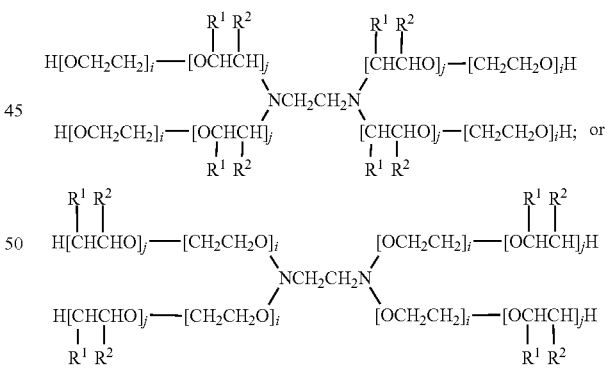

wherein for each $R^1$, $R^2$ pair, one is hydrogen and the other is a methyl group.

The particularly preferred copolymers are the pluronic where both hydrophobic and hydrophilic copolymers in the copolymer mixture have the formula:

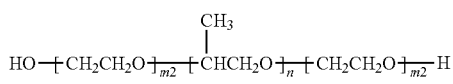

Of course, the ordinarily skilled artisan will recognize that the values of m and n will usually represent a statistical average and that the number of repeating units of the first block of a given molecule will generally not be exactly the number of repeating units of the third block. The characteristics of a number of pluronics are as follows:

| Copolymer | Hydrophobe weight | CMC (% w/v) | Hydrophobe percentage |
|---|---|---|---|
| Pluronic L61 | 1750 | 0.0003 | 90 |
| Pluronic L64 | 1750 | 0.002 | 60 |
| Pluronic F68 | 1750 | 4-5 | 20 |
| Pluronic P85 | 2250 | 0.005-0.007 | 30 |
| Pluronic F127 | 4000 | 0.003-0.005 | 30 |
| Pluronic F108 | 3250 | 0.0035-0.007 | 30 |

These CMC values were determined by the tension method described in Kabanov et al., Macromolecules 28:2303-2314 (1995).

Additional specific poly(oxyethylene)-poly(oxypropylene) block copolymers relevant to the invention include:

| Pluronic | Hydrophobe Weight | Hydrophobe Percentage |
|---|---|---|
| L31 | 950 | 90% |
| F35 | 950 | 50% |
| L42 | 1200 | 80% |
| L43 | 1200 | 70% |
| L44 | 1200 | 60% |
| L61 | 1750 | 90% |
| L63 | 1750 | 80% |
| L63 | 1750 | 70% |
| P65 | 1750 | 50% |
| F68 | 1750 | 20% |
| L72 | 2050 | 80% |
| P75 | 2050 | 50% |
| L81 | 2250 | 90% |
| P84 | 2250 | 60% |
| P85 | 2250 | 50% |
| F87 | 2250 | 30% |
| F88 | 2250 | 20% |
| L92 | 2750 | 80% |
| F98 | 2750 | 20% |
| P103 | 3250 | 70% |
| P104 | 3250 | 60% |
| P105 | 3250 | 50% |
| F108 | 3250 | 20% |
| L121 | 4000 | 90% |
| L122 | 4000 | 80% |
| L123 | 4000 | 70% |
| F127 | 4000 | 30% |
| 10R5 | 1000 | 50% |
| 10R8 | 1000 | 20% |
| 12R3 | 1200 | 70% |
| 17R2 | 1700 | 80% |
| 17R2 | 1700 | 80% |
| 17R4 | 1700 | 60% |
| 17R8 | 1700 | 20% |
| 22R4 | 2200 | 60% |
| 25R1 | 2500 | 90% |
| 25R2 | 2500 | 80% |
| 25R4 | 2500 | 60% |
| 25R5 | 2500 | 50% |
| 25R8 | 2500 | 50% |
| 31R1 | 3100 | 90% |
| 31R2 | 3100 | 80% |
| 31R4 | 3100 | 60% |

From the pluronics given above, the preferred hydrophilic polymer for use in the formulation of this invention is Pluronic F127 and the preferred hydrophobic copolymer is Pluronic L61.

In accordance with this invention the new and unexpected results are achieved by formulating the composition prior to drying by adding lactose to the composition. It is the addition of lactose in combination with the copolymer mixture of polyoxyethylene-polyoxypropylene copolymers that allows the composition to be easily dried and reconstituted without substantially losing its pharmaceutical effectiveness. While various other sugars and polysaccharides have been tried, lactose is the only one of which solubilizes the doxorubicin composition and allows the composition to be reconstituted quickly and without loss of any pharmaceutical activity.

The lactose can be present in the composition in any amount which is at least sufficient to solubilize the composition containing doxorubicin or its pharmaceutically acceptable salts. Any amount of lactose which is at least sufficient to solubilize the doxorubicin component when water is added to this composition can be utilized in the composition of this invention or in formulating the injectable solution. Generally, the lactose is present in an amount of from about 2.5 parts by weight to about 25 parts by weight based upon the weight of the doxorubicin or its pharmaceutically acceptable salts in a composition.

The composition can contain conventional stabilizers suitable for injectable compositions. While any of these stabilizers can be utilized, if desired, in formulating the composition of this invention, the aforementioned beneficial stability results are best achieved by the use of methyl paraben as a stabilizer. Any amount of methyl paraben which is at least sufficient to stabilize the doxorubicin component in the composition or in the injectable formulation can be utilized in accordance with this invention. When methyl paraben is utilized in the composition of this invention, good results are achieved by the presence of methyl paraben in an amount of from about 0.1 to 10 parts by weight based upon the weight of doxorubicin in the composition. Other conventional excipients for pharmaceutical injectable compositions can be present in the formulation.

The formulation so prepared is dissolved in an aqueous medium. In preparing the formulation, any quantity of doxorubicin or pharmaceutically acceptable salts thereof can be utilized with the amount of the other ingredients in the composition being dependent upon the predetermined amount of doxorubicin or its pharmaceutically acceptable salts thereof present in the composition so formulated. In this manner the composition is prepared in bulk, with larger or smaller amounts of doxorubicin or its pharmaceutically acceptable salts than the therapeutically effective amount needed for use in chemotherapy. Providing the unit dosage forms for therapeutic administration can be done after the composition is dried and reconstituted for use just prior to administration by injection. On the other hand, the injectable solution containing the therapeutically effective amount of doxorubicin or its pharmaceutically acceptable salts can be prepared initially and after drying be reconstituted as a unit dosage form for injectable administration as a chemotherapeutic agent to cancer patients.

In the next step of the process the doxorubicin containing solution prepared above is dried to form a solid powder. Any conventional method of drying can be utilized to carry out this procedure. The preferred method of drying is freeze drying. In utilizing freeze drying any of the conventional techniques for carrying out this step can be utilized in accordance with this invention. After drying and forming the powder the powder can be reconstituted by addition of an aqueous injectable medium to form the solution for administration by injection or infusion. The solid material, so produced, can later be added to the sterile aqueous injectable medium, such as sterile pyrogene-free water, and the resulting solution may be combined or divided into unit dosage forms for injection. These unit dosage forms can contain, if desired, additional preservatives or stabilizers. These formulations for injection can be present in unit dosage forms such as vials, bottles or ampoules or in multi-dose containers or containers for continuous infusion.

The aqueous injectable formulations containing doxorubicin or its pharmaceutically acceptable salts can be administered to patients, particularly cancer patients, for chemotherapeutic purposes as an anti-tumor agent. In treating such patients the composition of this invention which is injected into the patient should contain an effective amount of doxorubicin or its pharmaceutically acceptable salts to treat tumors in cancer patients. In general, the compositions of this invention can be intravenously injected or infused so as to provide a unit dose of doxorubicin or its pharmaceutically acceptable salts of from about 30 mg to about 80 mg per square meter administered every two to four weeks. Generally it is preferred that this unit dose of doxorubicin or its pharmaceutically acceptable salts be administered once every three weeks. This can be achieved by providing a unit dose as an injectable solution containing from about 16 mg to about 200 mg of doxorubicin or its pharmaceutically acceptable salts. Any amount of doxorubicin or its pharmaceutically acceptable salts which can be effective administered by injection in a unit dose for chemotherapy can be used in the injectable compositions of this invention. It must be understood that the precise dosage by intravenous therapy necessary will vary with age, size, sex and conditions of the subject as well as the severity of the disorder to be treated and the like and be subject to the physician's discretion.

The injectable composition of this invention containing doxorubicin or its pharmaceutically acceptable salts will act as a chemotherapeutic anti-tumor agent in the same manner as doxorubicin and its pharmaceutically acceptable salts. As is known, doxorubicin, as well as its pharmaceutically acceptable salts, have wide anti-tumor activity and are used in chemotherapy to combat and treat various tumors. In the same manner, the injectable composition of this invention can be used for this purpose. Due to the improved solubility of doxorubicin and its pharmaceutically acceptable salts, by means of the formulation of this invention, improved efficacy of the drug can be obtained.

EXAMPLES

Examples 1 and 2 are directed to demonstrating that lactose, and not other sugars, provides the aqueous solubility to doxorubicin compositions containing mixtures of hydrophobic/hydrophilic polyoxyethylene polypropylene block copolymers.

Example 3 demonstrates the enhanced solubility of these compositions of this invention containing lactose.

Example 1

Preparation of Solid Formulations

The weighted amounts of formulation components prescribed in the table below were placed in glass flask. 0.5 L of water was added to the flask, and the mixture was slowly mixed until homogenous. The mixture was filtered, and transferred to glass vials, 0.5 mL per vial. The liquid in bottles was frozen to below −30 degree C., and freeze-dried using EZ585R system (FTS), at pressure below 0.15 Torr, for 24 hours, and sealed. The product was a solid pellet containing 2.0 mg doxorubicin per vial.

In the table given below "Formulation ID" refers to the identification number of the formulations.

| Formulation ID | Components | Amounts used for preparation [g] |
|---|---|---|
| F1 | Doxorubicin | 2 |
|  | Pluronic F127 | 20 |
|  | Pluronic L61 | 2.5 |
| F2 | Doxorubicin | 2 |
|  | Pluronic F127 | 20 |
|  | Pluronic L61 | 2.5 |
|  | NaCl | 9 |
| F3 | Doxorubicin | 2 |
|  | Pluronic F127 | 20 |
|  | Pluronic L61 | 2.5 |
|  | Dextrose | 20 |
| F4 | Doxorubicin | 2 |
|  | Pluronic F127 | 20 |
|  | Pluronic L61 | 2.5 |
|  | Dextrose | 50 |
| F5 | Doxorubicin | 2 |
|  | Pluronic F127 | 20 |
|  | Pluronic L61 | 2.5 |
|  | Sucrose | 10 |
| F6 | Doxorubicin | 2 |
|  | Pluronic F127 | 20 |
|  | Pluronic L61 | 2.5 |
|  | Sucrose | 20 |
| F7 | Doxorubicin | 2 |
|  | Pluronic F127 | 20 |
|  | Pluronic L61 | 2.5 |
|  | Sucrose | 50 |
| F8 | Doxorubicin | 2 |
|  | Pluronic F127 | 20 |
|  | Pluronic L61 | 2.5 |
|  | Lactose | 20 |
| F9 | Doxorubicin | 2 |
|  | Pluronic F127 | 20 |
|  | Pluronic L61 | 2.5 |
|  | PEG5000 | 10 |
| F10 | Doxorubicin | 2 |
|  | Pluronic F127 | 20 |
|  | Pluronic L61 | 2.5 |
|  | PEG5000 | 20 |
| F11 | Doxorubicin | 2 |
|  | Pluronic F127 | 20 |
|  | Pluronic L61 | 2.5 |
|  | PEG5000 | 10 |
|  | Sucrose | 10 |
| F12 | Doxorubicin | 2 |
|  | Pluronic F127 | 20 |
|  | Pluronic L61 | 2.5 |
|  | Lactose | 20 |
|  | Methyl paraben | 2 |
| F13 | Doxorubicin | 2 |
|  | Pluronic F127 | 20 |
|  | Pluronic L61 | 2.5 |
|  | Lactose | 20 |
|  | Methyl paraben | 2 |
|  | NaCl | 9 |

Example 2

Dissolution of Formulations

The solid formulation prepared according to the Example 1 were reconstituted by adding to the vials 1 mL of water or 1 mL of saline (0.9% NaCl solution in pure water), as prescribed in the table below, to obtain solution of 2 mg/mL of doxorubicin in aqueous isotonic (0.9%) NaCl. The solubility of all of the samples were tested by mixing the samples on 180 degree shaker set to 120 rpm. The dissolution process was inspected visually. The time necessary to obtain clear solution is noted in the table. Only dissolution times of 1 minute or less were considered satisfactory.

TABLE

| Formulation ID | Dissolution medium | Time to dissolution |
| --- | --- | --- |
| F1 | saline | 10 |
| F2 | water | 3 |
| F3 | saline | 2 |
| F4 | saline | 2 |
| F5 | saline | 2 |
| F6 | saline | 3 |
| F7 | saline | 4 |
| F8 | saline | 1 |
| F9 | saline | 4 |
| F10 | saline | 3 |
| F11 | saline | 2 |
| F12 | saline | 1 |
| F13 | water | 1 |

As seen from the above table only the formulations F8, F12 and F13, the compositions which contained lactose, had acceptable dissolution properties of 1 minute or less in an aqueous medium.

Example 3

Chemical Stability of Doxorubicin in Formulations

The chemical stability of the solid formulations prepared according to the Example 1 were tested by storing these samples in glass vials which were sealed and allowed to stand at 25 degree for 4 months. Subsequently the samples were reconstituted by adding 1 mL of water or saline (0.9% NaCl solution in pure water), as described in the Example 2, and yielded clear solutions.

Stability of each of the samples was defined by evaluating the concentration of doxorubicin in the reconstituted samples by HPLC in the following manner. The formulation samples were diluted with 0.9% aqueous NaCl solution. 0.020 mL of the samples were injected into Symmetry Shield RP18 3.5 μm, 4.6 mm×50 mm column, and eluted with 0%-80% gradient of aqueous acetonitrile containing 0.1% trifluoroacetic acid. Eluate was analyzed by optical density at 225 nm. The content of doxorubicin in samples was determined by comparison of the area under the peak with that of respective standard samples.

The concentration of doxorubicin in the reconstituted samples, as determined by the method given above, is listed in the Table below.

| Formulation ID | Concentration of doxorubicin [mg/mL] |
| --- | --- |
| F1 | 1.72 |
| F2 | 1.74 |
| F3 | 1.86 |
| F4 | 1.46 |
| F5 | 0.45 |
| F6 | 1.04 |
| F7 | 1.29 |
| F8 | 1.35 |

-continued

| Formulation ID | Concentration of doxorubicin [mg/mL] |
| --- | --- |
| F9 | 1.22 |
| F10 | 1.17 |
| F11 | 0.37 |
| F12 | 1.97 |
| F13 | 1.96 |

As seen from above, the addition of methyl paraben in F12 and F13 provided enhanced stability as demonstrated by the fact that these samples had a concentration of doxorubicin, after reconstitution, which was substantially the same as the starting concentration.

Example 4

Preparation of the Formulation for Clinical Use 200 mg of doxorubicin, 2 g of Pluronic F127, 250 mg of Pluronic L61, 2 g of lactose, and 200 mg of methyl paraben were dissolved in 50 mL of water. The solution was filtered through 0.22 μm filer, and transferred to a sterile 100 mL serum bottle (Wheaton, USA). The bottle was frozen at −40° C., and freeze-dried at 0.150 Torr for 48 hours, then closed with sterile rubber stopper. The product was stored in darkness at controlled temperatures 2-8° C. Before the use, 100 mL of 0.9% Sodium Chloride Injection Solution USP was added and mixed until complete dissolution of the solid.

Example 5

This study demonstrates the efficacy and safety of the formulation of Example 4 in patients with adenocarcinoma of the esophagus that was not resectable with curative intent. This constitutes an open label two-centre phase II window study of the formulation of Example 4 in first line treatment of patients with advanced metastatic adenocarcinoma of the esophagus. In this study, 22 patients are entered into the study. The primary objectives of this study are to determine the therapeutic activity of the formulation of Example 4 in patients with adenocarcinoma of the esophagus that was not resectable with curative intent and to determine the overall (complete and partial) response rate. The secondary objectives include determination of the rate of palliation of dysphagia, collection of quality of life data and determination of the safety profile of the formulation of Example 4.

Patients eligible for the study have to fulfill the following criteria: male or female over 18 years, written informed consent, have histologically proven adenocarcinoma of the esophagus, disease not considered to be resectable with curative intent either because of being locally advanced (T4) or because of the presence of distant metastases in lung, liver, bones, celiac nodes or local peritoneal invasion, measurable (≧2 cm) and/or evaluable disease judged by computed tomography scanning, able to swallow tablets, Karnofsky score ≧60 with an expected survival of 12 weeks, left ventricular ejection fraction within normal limits but absolutely not <50%, adequate renal, hepatic and bone marrow function, no blood transfusion within the previous 2 weeks, negative pregnancy test and an effective contraception method, no prior chemotherapy, no underlying illness likely to be a danger to being enrolled in the trial and expected co-operation of the patient for the treatment and follow-up obtained and documented. The prospective analysis plan also requires that only metastatic lesions could be assessable as target lesions.

The following additional exclusion criteria apply: prior radiotherapy to the primary tumor, prior history of myocardial infarction within 6 months of study entry, unstable angina pectoris, cardiac insufficiency (New York Heart Association Class III-IV) or uncontrolled arrhythmia at the time of inclusion, clinically significant active infections, other prior malignancies, except for cured non melanoma skin cancer or curatively treated in situ carcinoma of the cervix, other serious illness or medical condition, history of a psychological illness or condition which may interfere with the patients ability to understand the requirements of the study, receive an investigational new drug within the last 30 days, hypersensitivity to anthracycline therapy and any other condition which in the investigator's opinion does not make the patient a good candidate for the trial.

Response definitions are adjusted in the prospective study analysis plan to allow for separate analyses by both modified WHO criteria and the RECIST criteria and to include only metastatic target lesions. Response assessment using metastatic target lesion measurements alone (the target lesion response rate) and overall per cent change from baseline of bi-dimensional target lesions are also planned as exploratory analyses in the prospective analysis plan. Development of unequivocal new lesions subsequent to the baseline assessment mean that the patient's response status at that point become progressive disease for WHO and RECIST assessments.

Patients receive 75 mg/m$^2$ of the formulation of Example 4 every 3 weeks for 2 courses. Efficacy evaluable patients have metastatic disease, have completed 2 treatment courses of the formulation of Example 4 and have completed both baseline and at least one follow up assessment computed tomography scan. Confirmation scans for the duration of response of at least 4 weeks duration are performed after completion of 2 and 4 more treatment cycles.

Primary endpoint for analysis is the overall per protocol response rate to the formulation of Example 4 in efficacy evaluable patients. Secondary endpoints are the overall response rate in all treated patients and the target lesion response rate and the overall response rate by RECIST criteria in efficacy evaluable patients. Exploratory analyses include responses that remain unconfirmed by a second assessment, responses by patient and by lesion for site of disease, per cent change from baseline of bi-dimensional target lesions, and the overall response rate when the primary site lesions are included in the calculations.

Seventeen patients are evaluable for efficacy in the independent review and 18 patients in the case report form database. Twenty two patients are entered into the study and 21 receive at least one dose of the formulation of example 4 (the per protocol all treated efficacy population). Criteria for evaluating efficacy include placement of patients with measurable disease into response categories including complete and partial response, stable disease and progressive disease according to WHO or RECIST criteria. Additional categories of unconfirmed complete and partial response are also included.

The overall response rate is 47% (8 of 17 patients) in efficacy evaluable patients in the independent review. The overall response rate in all treated patients is 38% (8 of 21 patients). The overall response rate in efficacy evaluable patients by RECIST criteria is 41% (7 of 17 patients) and the target lesion response rate is 47% (8 of 17 patients). Per cent change from baseline of bi-dimensional target lesions: 82% (14 of 17 patients) show some degree of tumor shrinkage after completing 2 courses of treatment with THE formulation of example 4. Overall confirmed response rates by patient for site of disease for bi-dimensionally measured target lesions in efficacy evaluable patients are 0% for primary sites, 44% for liver metastases, 38% for lymph node metastases and 33% for the remaining metastatic sites. The overall target lesion response rate including primary site lesions in efficacy evaluable patients is 35% (6 of 17 patients).

The overall response rate of 39% (7 of 18 efficacy evaluable patients) in investigator data (case report form data) and 47% (8 of 17 efficacy evaluable patients) in the independent review are observed. Six of the 7 confirmed responses (86%) in the investigator (case report form) database are confirmed by the independent review.

A high overall response rate of 47% in metastatic disease is observed in the independent third party review in efficacy evaluable patients receiving first-line treatment with the formulation of example 4 for oesophageal adenocarcinoma. The overall response rate in all treated patients is 38%. The overall response rate of 39% in investigator data (case report form data) and 47% in the independent review are observed. Six of the 7 confirmed responses (86%) in the investigator (case report form) database are confirmed by the independent review. As seen from the results, the formulation of example 4 produced a high level of activity in this study in patients with oesophageal adenocarcinoma.

Example 6

This is a study to demonstrate the effectiveness of the formulation of Example 4 in second line treatment of patients with measurable metastatic adenocarcinoma of the esophagus or gastroesophageal junction. This is an open-label, prospective multicenter phase II trial. Thirty five efficacy evaluable patients are entered into the study. An interim response rate analyses is performed after 10 efficacy evaluable patients complete the study protocol.

The primary objective of this study is to estimate the objective response rate, defined as the proportion with partial response or complete response in patients with metastatic adenocarcinoma of the esophagus or gastroesophageal junction that are treated for 12 months with the formulation of Example 4 after having failed first line chemotherapy. The secondary objective of the study is to estimate the duration of objective response, duration of progression—free survival, overall clinical benefit rate, overall survival rate, change in the quality of life scales, safety and tolerability during the 12 month treatment period.

Patients with stable disease or better receive up to 6 three-weekly treatments until disease progression followed by a 4 week treatment completion visit. Six weekly assessment visits continue until disease progression. Survival status census is performed on a 12 weekly basis after disease progression. Clinical cut-off for the study analysis of overall response rate is 6 months after entry of the last non-progressing patient and for the survival analysis is 12 months after entry of the last surviving patient. Patients with adenocarcinoma of the esophagus or gastroesophageal junction with at least one measurable distant metastasis who have failed first line combination chemotherapy are enrolled. Out-patients ≧18 years with histologically confirmed esophageal or gastroesophageal cancer and informed consent are eligible. Patients have at least one unidimensionally measurable lesion.

Patients receive 65 mg/m$^2$ of the formulation of Example 4 intravenously every 3 weeks for a total of 6 courses of the formulation of Example 4 in the absence of disease progression or unacceptable toxicity. Written informed consent is obtained before any study-specific procedures. The following assessments are completed within 14 days prior to treatment: demographic data, complete medical history, complete physical examination, height and body weight, vital signs, pregnancy test for women of child-bearing potential, baseline assessment of dysphagia, Karnofsky performance status, New York Heart Association cardiac classification, chest X-ray, 12-lead electrocardiogram, left ventricular ejection fraction, hematology, blood chemistry and urinalysis. The baseline tumor assessment is evaluated by computed tomography scanning.

The following assessments are completed every 3 weeks during the first 2 cycles of treatment with the formulation of example 4: complete physical examination, body weight, performance status, vital signs, hematology, blood chemistry and urinalysis. A clinical assessment including adverse events review, concomitant medication, assessment of dysphagia and concurrent illness is also done. One week after the first administration of the formulation of example 4, patients are clinically evaluated (adverse events review, concomitant medication, assessment of dysphagia and concurrent illness) and the following laboratory evaluations are conducted: hematology, blood chemistry and urinalysis. Quality of life questionnaires are completed by patients at the start of the visit prior to any treatment being given at the baseline visit (Day 1/Cycle 1) and on Day 1 of Cycle 2.

Patients are seen on Day 22 of Cycle 2 to evaluate their response to the 2 courses of treatment with the formulation of example 4. The following tests are completed on that visit: complete physical examination, body weight, performance status, vital signs, hematology, blood chemistry and urinalysis. A clinical assessment including adverse event review, concomitant medication, assessment of dysphagia and concurrent illness is also done. Computed tomography scanning is done on Day 22 of Cycle 2 to assess tumor response after 2 courses of the formulation of example 4. Left ventricular ejection fraction evaluation is evaluated after 2 courses of treatment with the formulation of example 4.

Further to the review of results following computed tomography scanning, patients who have progressive disease after 2 courses of the formulation of example 4 may come off study. Patients with progressive disease are seen on Day 28 of Cycle 2 for a study termination visit and the following tests are completed: chest X-ray, electrocardiography and clinical assessment including adverse event review, concomitant medication, assessment of dysphagia and concurrent illness. Patients with progressive disease also complete quality of life questionnaires on Day 28 of Cycle 2 (termination visit). Those patients continue to be followed for survival and quality of life. They complete quality of life questionnaires one time during the standard chemotherapy treatment and at the completion of the treatment.

If after 2 courses of treatment with the formulation of example 4 there is stable disease or better, then up to 4 more courses of the formulation of example 4 may be given to patients. The third treatment course of the formulation of example 4 is given on Day 28 of Cycle 2. The following assessments are completed every 3 weeks during the second study part of treatment with the formulation of example 4: complete physical examination, body weight, performance status, vital signs, hematology, blood chemistry and urinalysis. A clinical assessment including adverse events review, concomitant medication, assessment of dysphagia and concurrent illness is also done. Tumor assessment by computed tomography scanning and left ventricular ejection fraction evaluation are performed every 6 weeks, e.g. at completion of cycles 4 and 6. Quality of life questionnaires are completed by patients at the start of the visit prior to any treatment being given at cycles 4 and 6.

Patients are seen 1 week after the last treatment cycle with the formulation of example 4 and the following tests are completed: complete physical examination, body weight, performance status, vital signs, chest X-ray, hematology, blood chemistry, urinalysis and electrocardiography. A clinical assessment including adverse events review, concomitant medication, assessment of dysphagia and concurrent illness is also done. Tumor assessment by computed tomography scanning is performed on Day 28 of the final cycle. Quality of life questionnaires are completed by the patients.

Patients discontinued from the study after 3 courses or more of treatment with the formulation of example 4 for any reason are asked to come for a study termination visit. The following parameters are assessed: complete physical examination, body weight, performance status, vital signs, chest X-ray, hematology, blood chemistry, urinalysis and electrocardiography. A clinical assessment including adverse events review, concomitant medication, assessment of dysphagia and concurrent illness is also done. Tumor assessment is performed at the study termination visit. Quality of life questionnaires are completed by the patients.

After completion of study treatment or after early withdrawal from study treatment, patients are followed every 2 months for up to 6 months or until death if it occurs earlier. The following parameters are assessed: complete physical examination, body weight, performance status, vital signs, adverse events review, concomitant medication, dysphagia, concurrent illness and tumor assessment by computed tomography scanning. Time to progression and survival status census are performed on a 6 weekly basis to completion of the study and thereafter every 12 weeks for those patients who stop treatment due to reasons other than disease progression. Survival status census is performed on a 12 weekly basis after disease progression.

The primary measure of efficacy in the current study is the overall response rate. Secondary efficacy outcome measures are target lesion response rate, duration of progression-free survival, survival of responders overall survival. Duration of the overall response, time to overall response, and overall clinical benefit rate and quality of life are also evaluated. Safety is assessed as the incidence of adverse events and toxicity evaluation.

Based upon the results, at the end of the study, a greater percentage of the patients in the group of patients treated with the formulation of Example 4 have clinical benefit including, but not limited to, at least one of the following endpoints: overall response rate, duration of overall response, time to overall response, duration of progression-free survival, overall clinical benefit rate, overall survival rate and quality of life.

What is claimed is:

1. A dry doxorubicin composition, wherein the dry composition dissolved in an injectable aqueous media, is suitable for administration by injection; said dry doxorubicin composition is produced by a process comprising the steps of:
   a) first forming a solution by dissolving in an aqueous medium:
      i) a predetermined amount of doxorubicin or pharmaceutically acceptable salt thereof;
      ii) a polyoxyethylene polyoxypropylene copolymer mixture, wherein the copolymer mixture contains two block copolymers, one of which is a hydrophobic copolymer having an ethylene oxide content of from about 10% to about 50% by weight of the copolymer mixture and the other block copolymer being a hydrophilic copolymer having an ethylene oxide content of from about 50% by weight to about 90% by weight of the copolymer mixture; and iii) from about 2.5 to 25 parts by weight of lactose, based upon the weight of the doxorubicin or its salts; and b) thereafter drying such solution.

2. The composition of claim 1 wherein drying step b is carried out by freeze drying.

3. An injectable unit dosage form of which comprises from about 16 mg to about 200 mg of the composition of claim 2 dissolved in a suitable injectable aqueous medium.

4. The injectable unit dosage form of claim 3, wherein said unit dosage form has a volume of from about 10 mL to about 500 mL.

5. The composition of claim 1, wherein said copolymer mixture in said composition is present in an amount of from about 4 parts to about 40 parts by weight of the doxorubicin or its salt in said composition.

6. The composition of claim 5, wherein the hydrophilic copolymer is present in an amount of from about 2 to about 20 per parts by weight of the hydrophobic copolymer.

7. The composition of claim 6, wherein the hydrophilic copolymer is present in an amount of 3 to 10 parts by weight per part by weight of the hydrophobic copolymer.

8. The composition of claim 6, wherein said composition contains from about 10 to about 15 parts by weight of the copolymer mixture based upon the weight of doxorubicin in the composition.

9. The composition of claim 8, wherein the block copolymers are selected from those represented by the formula:

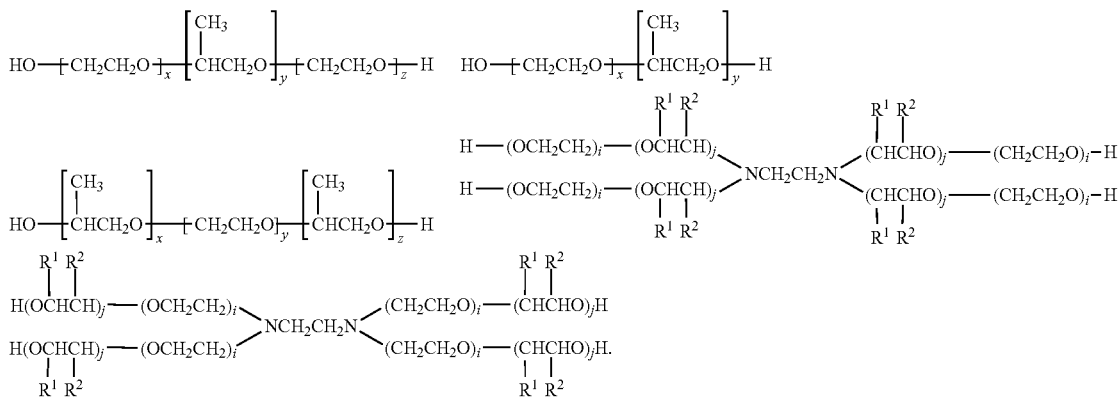

and wherein x, y, z, i and j have values from about 2 to about 800, and wherein, for each $R^1$, $R^2$ pair, one is hydrogen and the other is a methyl group.

10. The composition of claim 9, wherein both block copolymers are represented by the formula:

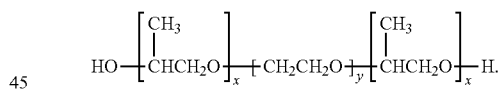

11. The composition of claim 1, wherein said composition contains methyl paraben in an amount at least sufficient to stabilize the doxorubicin or its pharmaceutically acceptable salt in said composition.

12. The composition of claim 11, wherein said composition contains methyl paraben in an amount of from about 0.1 parts by weight to 2 parts by weight based upon the weight of doxorubicin or its pharmaceutically acceptable salts.

13. A composition for delivering a doxorubicin to a patient comprising a therapeutically effective amount of the composition of claim 1.

14. The composition of claim 13, wherein said composition, upon dissolution in an injectable aqueous medium, is suitable for injectable administration to a patient.

15. The composition of claim 13 which comprises a therapeutically effective amount of the composition wherein drying step b is carried out by freeze drying.

16. An injectable liquid unit dosage form comprising from about 16 mg to about 200 mg of the composition of claim 1 dissolved in a suitable injectable aqueous medium.

* * * * *